US011457941B2

(12) United States Patent
Lin et al.

(10) Patent No.: US 11,457,941 B2
(45) Date of Patent: Oct. 4, 2022

(54) ARTICULABLE ENDOSCOPIC INSTRUMENTS

(71) Applicant: The Regents of the University of California, Oakland, CA (US)

(72) Inventors: Matthew Lin, San Francisco, CA (US); Dillon Kwiat, San Francisco, CA (US); Neil Ray, San Francisco, CA (US); Stanley Rogers, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 396 days.

(21) Appl. No.: 16/084,603

(22) PCT Filed: Mar. 15, 2017

(86) PCT No.: PCT/US2017/022592
§ 371 (c)(1),
(2) Date: Sep. 13, 2018

(87) PCT Pub. No.: WO2017/161049
PCT Pub. Date: Sep. 21, 2017

(65) Prior Publication Data

US 2019/0076160 A1 Mar. 14, 2019

Related U.S. Application Data

(60) Provisional application No. 62/463,351, filed on Feb. 24, 2017, provisional application No. 62/308,786, filed on Mar. 15, 2016.

(51) Int. Cl.

| | |
|---|---|
| ***A61B 17/29*** | (2006.01) |
| ***A61B 17/00*** | (2006.01) |
| *A61B 1/00* | (2006.01) |

(52) U.S. Cl.
CPC .... *A61B 17/2909* (2013.01); *A61B 17/00234* (2013.01); *A61B 17/29* (2013.01);
(Continued)

(58) Field of Classification Search
CPC combination set(s) only.
See application file for complete search history.

(56) References Cited

U.S. PATENT DOCUMENTS

2007/0276430 A1* 11/2007 Lee ........................ A61B 17/29 606/205
2010/0249497 A1 11/2010 Peine
(Continued)

FOREIGN PATENT DOCUMENTS

WO 2015033607 A1 3/2015

OTHER PUBLICATIONS

International Search Report for PCT/US17/22592 dated Jul. 11, 2017.
(Continued)

*Primary Examiner* — Anh T Dang
(74) *Attorney, Agent, or Firm* — Thomas | Horstemeyer, LLP

(57) ABSTRACT

In one embodiment, an articulable endoscopic instrument including an articulable retractor configured to pass through a working channel of an endoscope, the articulable retractor including an end effector mounted to a distal end of the articulable retractor, and a handle to which the articulable retractor is mounted, the handle comprising controls that enable a user of the instrument to both articulate the retractor and actuate the end effector, wherein the retractor can be articulated using the controls to form two independent bends lying within one plane, the bends together forming a complex curve.

9 Claims, 5 Drawing Sheets

(52) U.S. Cl.
CPC ... *A61B 1/00087* (2013.01); *A61B 2017/0034* (2013.01); *A61B 2017/00314* (2013.01); *A61B 2017/00327* (2013.01)

(56) References Cited

U.S. PATENT DOCUMENTS

2012/0116415 A1 5/2012 Forsell
2012/0310220 A1* 12/2012 Malkowski ........... A61B 17/29 606/1

OTHER PUBLICATIONS

Chellali, A., and Cao, C., 2013, "The Impact of New Instruments on Surgical Performance in Natural Orifice Translumenal Endoscopic Surgery," Proceedings of the Human Factors and Ergonomics Society Annual Meeting, San Diego, CA, 57, pp. 663-667.
Tessier, C., Zhang, L., and Cao, C., 2012, "Ergonomic Considerations in Natural Orifice Translumenal Endoscopic Surgery (NOTES): A Case Study," Work: A Journal of Prevention, Assessment and Rehabilitation, 41(1), pp. 4683-4688.
Von Rentein, D., Vassiliou, M., Rosch, T., and Rothstein, R., 2011, "Triangulation: Holy Grail of Endoscopic Surgery?" Surg Endosc, 25(1), pp. 1355-1357.
Maple, J.T., Dayyeh, B., Chauhan, S., Hwang, J., Komanduri, S., Manfredi, M., Konda, V., Murad, F., Siddiqui, U., and Banerjee, S., 2015, "Endoscopic Submucosal Dissection," Gastrointestinal Endoscopy, 81(6), pp. 1311-1325.
Parretta, S., Dallemagne, B., Barry, B., and Marescaux, J., 2013, "The ANUBISCOPE® Flexible Platform Ready for Prime Time: Description of the First Clinical Case" Surg Endosc 27, pp. 2630.
Fuchs, K., and Breithaupt, W., 2012, "Transgastric Small Bowel Resection with the New Multitasking Platform EndoSAMURAI™ for Natural Orifice Transluminal Endoscopic Surgery," Surg Endosc. 26(8), pp. 2281-2287.
Centers of Disease Control, 2015, "CDC Statement: Los Angeles County/UCLA Investigation of CRE Transmission and Duodenoscopes," https://www.cdc.gov/hai/outbreaks/cdcstatement-la-cre.html, 4 pages.
Food and Drug Administration, 2015, "Design of Endoscopic Retrograde Cholangiopancreatography (ERCP) Duodenoscopes May Impede Effective Cleaning: FDA Safety Communication," http://www.fda.gov/MedicalDevices/Safety/AlertsandNotices/ucm434871.htm, 7 pages.
Chung, H., Dhumane, P., Liu, K., Donatelli, G., Dallemagne, B., and Marescaux, J., 2014, "Endoscopic Submucosal Dissection with a Novel Traction Method Using a Steerable Grasper: A Feasibility Study in a Porcine Model", Surgical Innovation, 21(1), pp. 5-10.
Chung, H., Diana, M., Liu, K., Dallemagne, B., and Marescaux, J., 2015, "East Meets West—A Novel Steerable Grasper to Facilitate Gastric Endoscopic Submucosal Dissection (ESD): Randomized Comparative Study in a Porcine Model.", Surgical Innovation, 22(2), pp. 117-122.
Feussner, H., Becker, V., Baur, M., Kranzfelder, M., Schirren, R., Lüth, T., Meining, A., and Wilhelm, D., 2015, "Developments in Flexible Endoscopic Surgery: A Review", Clinical and Experimental Gastroenterology, 8, pp. 31-42.
Boston Scientific, 2014, "Single-Use Radial Jaw 4," http://www.bostonscientific.com/en-US/products/forceps/single-use-radial-jaw-4-biopsy-forceps.html, 4 pages.

* cited by examiner

ARTICULABLE ENDOSCOPIC INSTRUMENTS

CROSS-REFERENCE TO RELATED APPLICATIONS

This application is the 35 U.S.C. § 371 national stage application of PCT Application No. PCT/US2017/022592, filed Mar. 15, 2017, where the PCT claims the benefit of and priority to U.S. Provisional Application Ser. No. 62/463,351, filed Feb. 24, 2017, and U.S. Provisional Application Ser. No. 62/308,786, filed Mar. 15, 2016, both of which are hereby incorporated by reference in their entireties.

BACKGROUND

Surgical endoscopy is a form of minimally invasive surgery that uses natural orifices to conduct therapeutic interventions, such as removal of benign and early malignant lesions in the gastrointestinal tract. Endoscopes comprise working channels, typically ranging from 2.8 mm to 6 mm in diameter, that enable the surgeon to access the surgical site within the body with endoscopic instruments designed to pass through the channels. Endoscopes often comprise two or more such channels so as to enable multiple endoscopic instruments to be used at the same time.

Although endoscopy provides many benefits, such as shortened hospital stays, reduced patient discomfort, and decreased overall healthcare costs, it also suffers from several challenges. One of the most significant of these challenges is the difficulty in achieving triangulation. In mathematics, triangulation is the process of identifying the location of a target point by forming triangles to the point from known locations. In endoscopy, triangulation refers to the process of identifying and accessing target tissue for the purpose of applying traction and counter-traction to the tissue to create a dissection plane in which an incision can be made. Unfortunately, it is difficult to achieve triangulation with most endoscopic instruments because they cannot be independently articulated. Instead, they typically can only be linearly extended from the endoscope and indirectly articulated by articulating the endoscope. As a result, the surgeon must manipulate the endoscope instead of the endoscopic instruments to create an appropriate dissection plane. This typically interferes with visualization of the dissection plane and, therefore, makes it more difficult for perform the surgical procedure.

From the above discussion, it can be appreciated that it would be desirable to have articulable endoscopic instruments that can be passed through the working channels of an endoscope and used to triangulate on target tissue.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have articulable endoscopic instruments that can be passed through the working channels of an endoscope and used to triangulate on target tissue. Disclosed herein are examples of such instruments. In some embodiments, an articulable endoscopic instrument comprises an articulable retractor that can be controlled using a handle to which the retractor is mounted. Mounted to a distal end of the retractor is an end effector that can be used to perform a particular action on target tissue accessed with the endoscope. The handle is designed so as to be usable with one hand to both articulate the retractor and actuate the end effector. In some embodiments, the orientations of the retractor and the end effector can be locked using controls of the handle.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
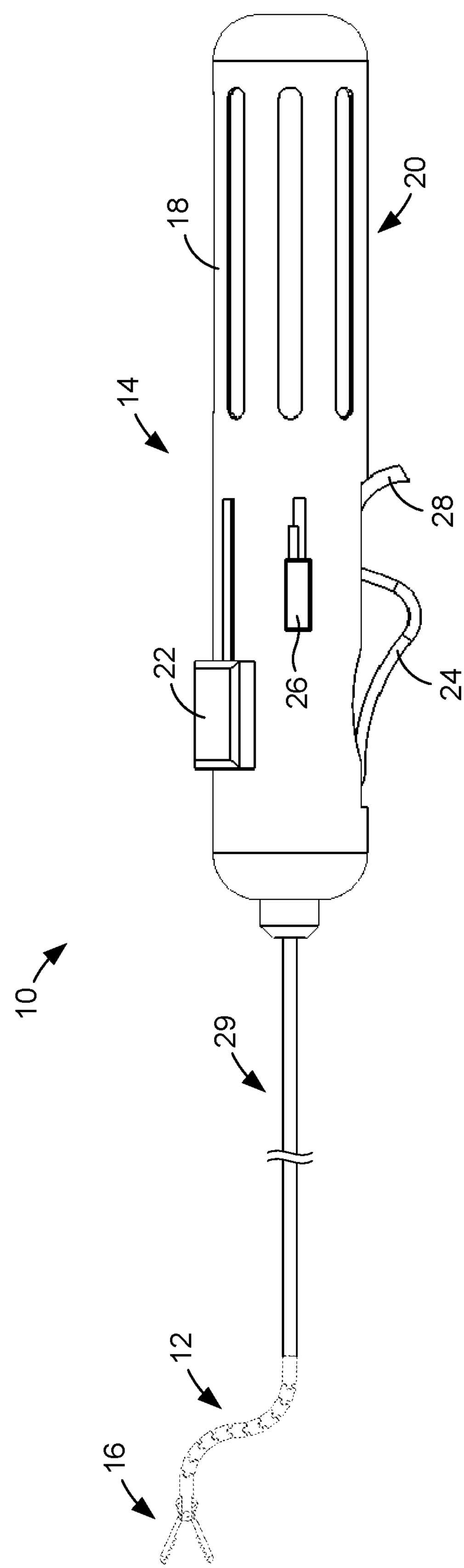
FIG. 1 is a side view of an embodiment of an articulable endoscopic instrument that can be used in conjunction with an endoscope.

FIG. 1 illustrates an articulable instrument 10 that can be used in conjunction with an endoscope having one or more working channels. As shown in FIG. 1, the instrument 10 generally comprises an articulable retractor 12 that is configured to be passed through an endoscope working channel and a handle 14 to which the retractor is mounted and that can be used to control operation of the retractor. Mounted to the distal end of the retractor 12 is an end effector 16 that can be used to perform a particular action on a target tissue accessed using the endoscope.

In the illustrated embodiment, the handle 14 comprises an elongated cylindrical housing 18 that can be held in and controlled with one hand to enable single-handed operation of the instrument 10. The handle 14 comprises a grip 20 located at a proximal end of the housing 18 and multiple controls distal of the grip that extend from the housing. These controls include thumb slides 22 (only the left-side thumb switch which being visible in FIG. 1) that can be used to articulate (i.e., bend) the retractor 12 and a finger trigger 24 that can be used to actuate the end effector 16. Each of these controls connect to internal control wires that link the controls to the controlled components. The controls of the handle 14 further include locking elements in the form of a thumb slide locking element 26 that can be used to lock the position of the thumb slide 22 and, therefore, the orientation of the retractor 12, and a finger trigger locking element 28 that can be used to lock the position of the finger trigger 24 and, therefore, the orientation of the end effector 16. Operation of these controls is described below in relation to FIGS. 3, 4, 8, and 9.

Connecting the retractor 12 and the handle 14 is an elongated tube 29 that can also pass through the endoscope working channel. The internal control wires that are used to control the retractor 12 and its end effector 16 pass through this tube 16. An embodiment for the tube 29 is described in relation to FIG. 7. By way of example, the tube 29 can have an outer diameter, or other maximum cross-sectional dimension, of no more than approximately 6 mm. In some embodiments, the tube 29 has an outer diameter, or other maximum cross-sectional dimension, of less than approximately 3 mm.

Figure 2:
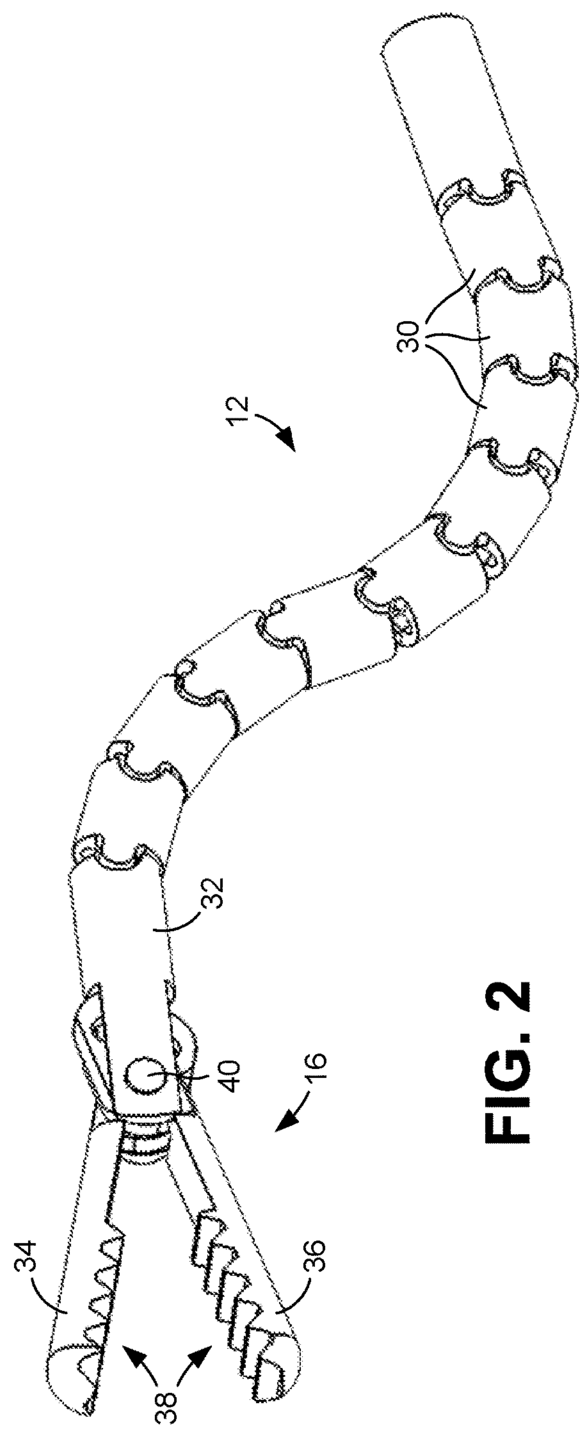
FIG. 2 is a perspective view of an embodiment of an articulable retractor of the instrument of claim 1.

FIG. 2 illustrates the articulable retractor 12, which can be made of a suitable, biocompatible material, such as stainless steel. As shown in this figure, the retractor 12 comprises an elongated shaft that is comprised by multiple medial articulable links 30, which are described below in relation to FIGS. 5 and 6. As is apparent from FIG. 2, the retractor 12 is capable of forming two distinct bends (i.e., a compound curve) both within the same plane. Each bend can be made using one of two internal control wires that are used to articulate the retractor 12. In some embodiments, each of the bends can form a full 90-degree bend that extend in opposite directions so as to form the S-shaped complex curve shown in FIG. 2.

Also shown in FIG. 2 is the end effector 16, which connects to the retractor 12 with a distal articulable link 32, which is described below in relation to FIG. 4. In the illustrated embodiment, the end effector 16 comprises a grasper having two opposed jaw elements 34 and 36. The jaw elements 34, 36 include intermeshing teeth 38 and are pivotally connected to each other at a pivot point with a pin 40, which also mounts the jaws to the distal articulable link 32. Although the end effector 16 is illustrated and described herein as being a grasper, it is noted that alternative endoscopic end effectors could be used.

Figure 3:
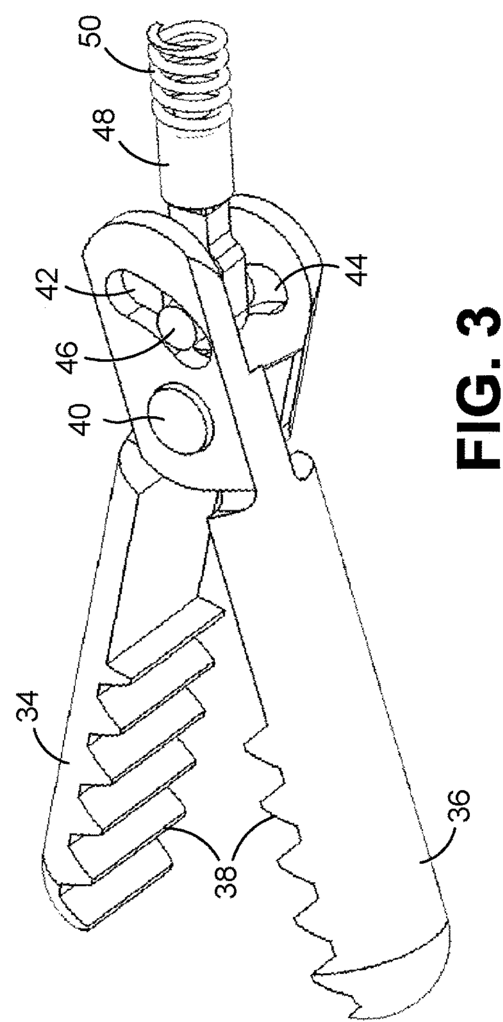
FIG. 3 is a perspective view of an embodiment of an end effector mounted to the retractor of FIG. 2.

FIG. 3 shows the components with which the jaw elements 34, 36 of the grasper can be actuated. As shown in this figure, each jaw element 34, 36 is provided with a curved slot 42 and 44 proximal of the pin 40 through which a further pin 46 of an actuation member 48 extends. The actuation member 48 comprises a small shaft that can be linearly translated within the distal articulable link 32 (FIG. 2) using one of the internal control wires of the instrument 10. In particular, when a control wire attached to the proximal end of the actuation member 48 is pulled in the proximal direction, the pin 46 travels proximally along the slots 42, 44 so as to close the jaw elements 34, 36. However, when that control wire is pushed in the distal direction, the pin 46 travels distally along the slots 42, 44 so as to open the jaw elements 34, 36.

As is further shown in FIG. 3, a compression spring 50 is provided at the proximal end of the actuation member 48 that urges the member toward the distal direction, thereby urging the jaw elements 34, 36 toward their open orientation, which is the default position for the grasper. Notably, the jaw elements 34, 36 are sized such that, when they are in the closed orientation, they can pass through the working channels of most endoscopes. By way of example, when the jaw elements 34, 36 are closed the end effector 16 has an outer diameter, or other maximum cross-sectional dimension, of no more than approximately 6 mm. In some embodiments, the end effector 16 has an outer diameter, or other maximum cross-sectional dimension, of less than approximately 3 mm when the jaw elements 34, 36 are closed.

Like the articulable links 32, 34 of the retractor 16, the various components of the end effector 16 can also be made of a suitable, biocompatible material, such as stainless steel.

Figure 4:
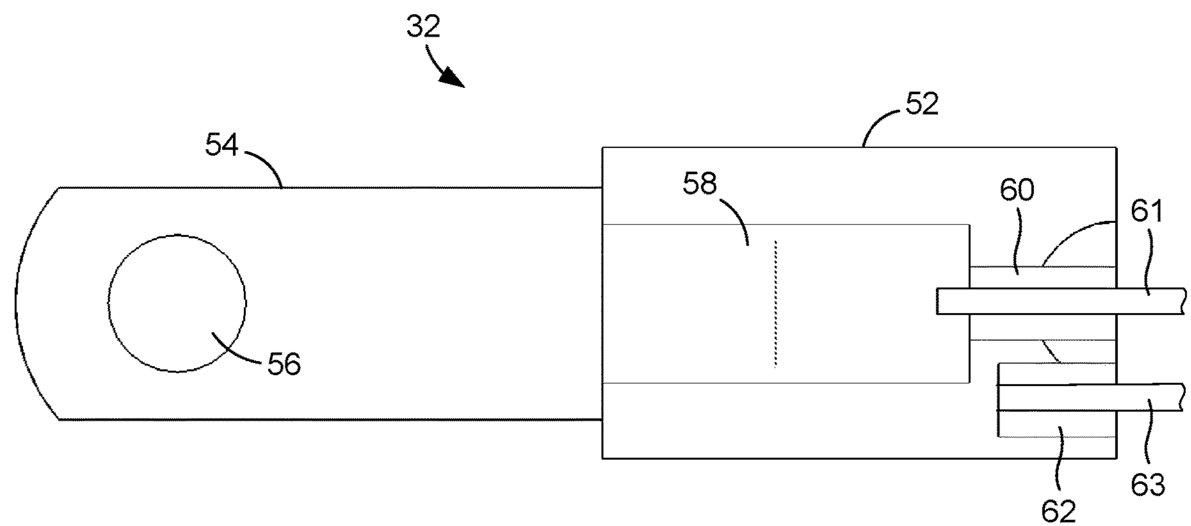
FIG. 4 is a cross-sectional side view of an embodiment of a distal articulable joint of the retractor of FIG. 2 to which the end effector of FIG. 3 mounts.

FIG. 4 shows the interior of the distal articulable link 32 of the retractor 12. As is apparent from this figure, the link 32 includes a body 52 from which extends opposed lateral prongs 54 between which the jaw elements 34, 36 can be positioned. The prongs 54 include openings 56 that are configured to receive the pin 40 about which the jaw elements 34, 36 pivot. Formed within the body 52 of the distal link 32 is a first cylindrical cavity 58 that is configured to receive the actuation member 48 and the spring 50. Extending from the proximal end of the body 52 to the first cavity 58 is a passage 60 through which an end effector control wire 61 can pass to connect with the actuation member 48 and control operation of the jaw elements 34, 36. Also formed in the body 52 is a second cylindrical cavity 62 that is configured to receive a retractor control wire 63 that attaches to the link 32 and that can be linearly displaced used to control articulation of the link and, therefore, the retractor 12.

Figure 5:
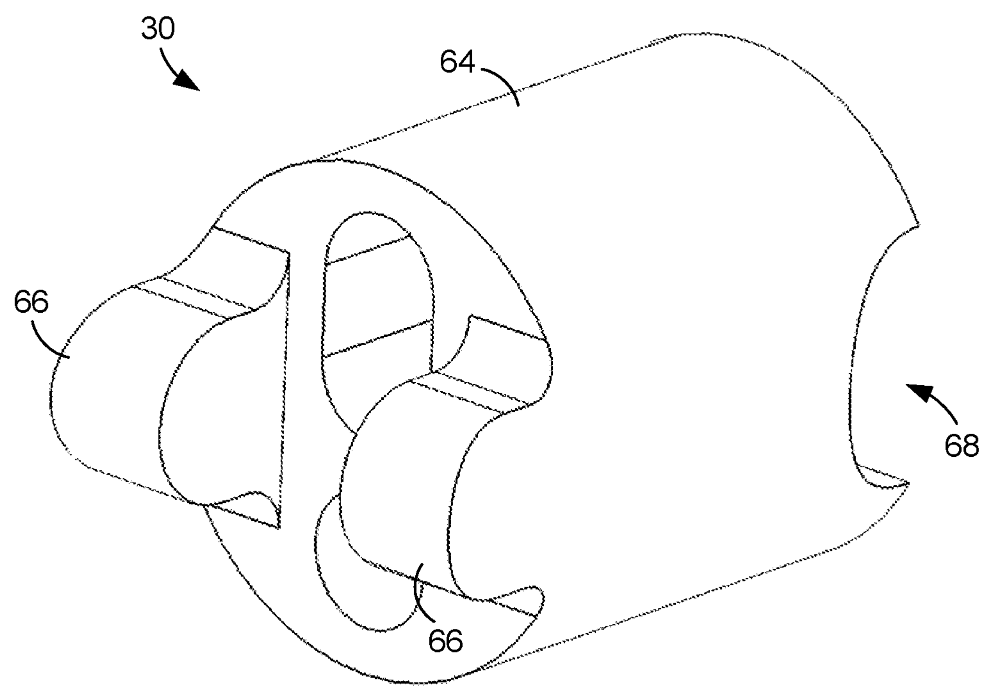
FIG. 5 is a distal perspective view of an embodiment of a medial articulable joint of the retractor of FIG. 2.
Figure 6:
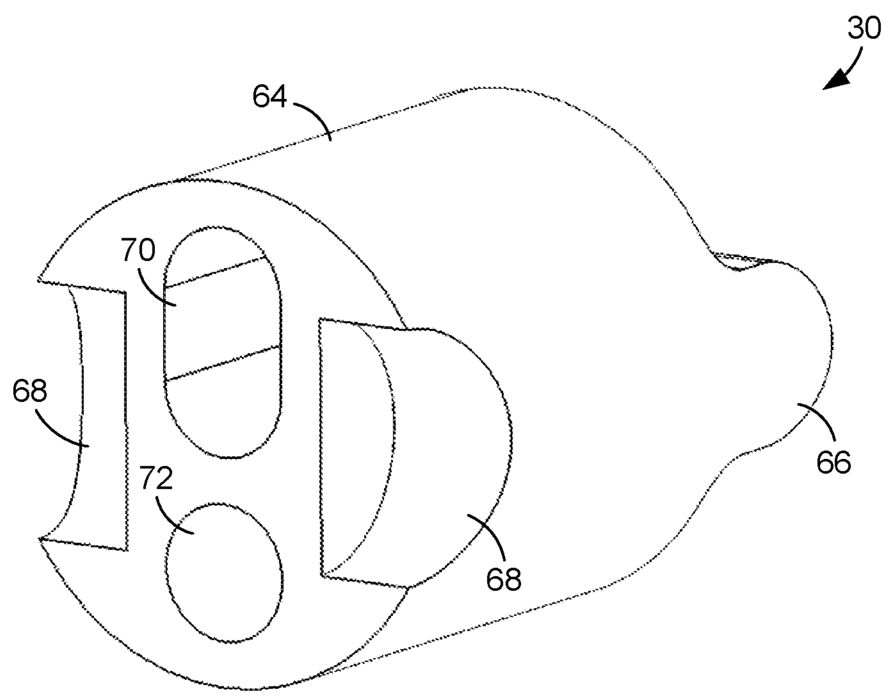
FIG. 6 is a proximal perspective view of the articulable joint of FIG. 5.

FIGS. 5 and 6 illustrate an example configuration for the medial articulable links 30 shown in FIG. 2. The link 30 comprises a cylindrical body 64. Extending from the distal end of the body 64 are two opposed lateral flanges 66 that are configured to facilitate connection with and articulation between a further, distally positioned link. Provided at the proximal end of the body 64 are two opposed lateral notches 68 that are configured to receive the flanges of a further, proximally positioned link. In some embodiments, the flanges 66 are simply received in the notches 68 and the links 30 are held together by tension provided by the control wires. In other embodiments, suitable attachment means, such as pins or snap-fit elements, can be used to ensure the links 30 cannot separate from each other. Like the end effector 16, the links 30 are dimensioned such that the retractor 12 can pass through the working channels of most endoscopes. By way of example, the links 30 each have an outer diameter, or other maximum cross-sectional dimension, of no more than approximately 6 mm. In some embodiments, the links 30 each have an outer diameter, or other maximum cross-sectional dimension, of less than approximately 3 mm.

With particular reference to FIG. 6, passages 70 and 72 are formed through the body 62 of the link 30. In the illustrated embodiment, the first passage 70 has an elongated cross-section while the second passage 72 has a circular cross-section. Irrespective of their shapes, the passages 70, 72 are configured to receive the control wires 61, 63 that are used actuate the jaw elements 34, 36 and to articulate the retractor 12. In some embodiments, the end effector control wire 61 that actuates the jaw elements 34, 36 passes through the second passage 72, while the retractor control wires 63 that articulate the retractor 12 pass through the first passage 70.

Figure 7:
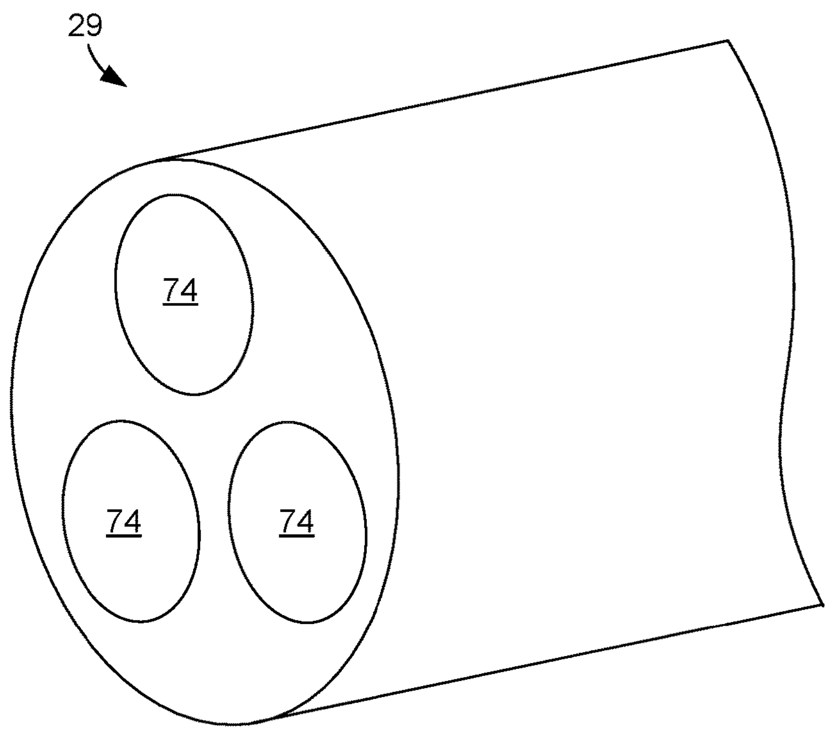
FIG. 7 is a partial perspective view of an embodiment of a tube shown in FIG. 1 that connects the retractor to the handle.

As noted above, the retractor 12 connects to the handle 14 with the elongated tube 29 (see FIG. 1). FIG. 7 shows an example embodiment for this tube 29. As shown in FIG. 7, the tube 29 is an elongated cylindrical member having multiple (e.g., three) passages 74 that extend through the tube. Each of these passages 74 can receive one of the control wires 61, 63 that extends from the handle 14 to the retractor 12. The tube 29 can be made of a suitable, biocompatible material, such as a polytetrafluoroethylene (PTFE).

Figure 8:
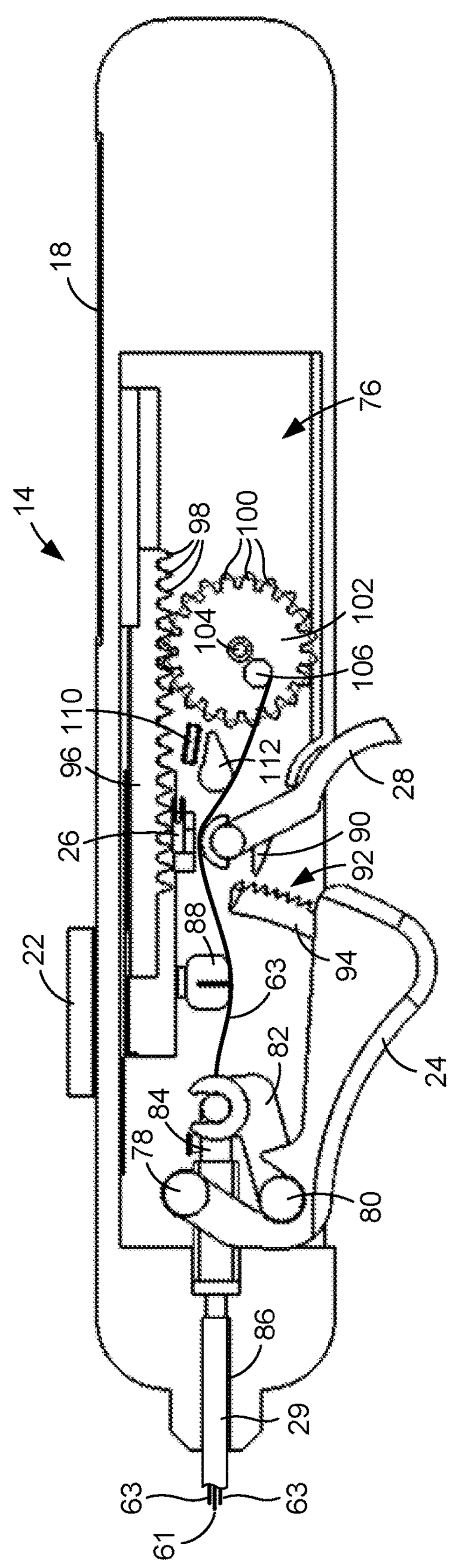
FIG. 8 is cross-sectional side view of an embodiment of the handle shown in FIG. 1.

FIG. 8 illustrates the handle 14 in cross-section. As the cross-section is taken along a medial plane of the handle 14, FIG. 8 shows one half (the right half in this case) of the handle. As indicated in the figure, a cavity 76 is formed within the handle 14 that houses various internal components of the handle. The finger trigger 24 is pivotally mounted within the cavity 76 at a pivot point 78. A notch 80 is formed within the body of the trigger 24 that receives the distal end of a linking element 82 that connects the trigger to a further actuation member 84 that is used to control actuation of the jaw elements 34, 36. Like the actuation member 84 shown in FIG. 3, the actuation member 84 is connected to the end effector control wire 61, which passes through the elongated tube 29. As is apparent in FIG. 8, the tube 29 is received within a cylindrical cavity 86 formed in a distal end of the handle 14. When the trigger 24 is squeezed such that it is moved toward the handle 14, the pivotal motion of the trigger is translated into linear motion of the actuation member 48 by the linking element 82 such that the end effector control wire 61 is moved proximally and the jaw elements 34, 36 are closed. In some embodiments, a compression spring (not shown) extends down from a protrusion 88 formed within the handle 14 to the inner side of the trigger 24 to urge the trigger outward. In such a case, when the trigger 24 is released, the trigger is pivoted outward, the actuation member 84 is moved in the distal direction, the end effector control wire 61 is also moved in the distal direction, and the jaw elements 34, 36 are opened.

As noted above, the finger trigger 24 can be locked in any desired position to fix the orientation of jaw elements 34, 36. This is achieved using the trigger locking element 28. As shown in FIG. 8, the trigger locking element 28 is a pivotally mounted lever having a distal tang 90 that can engage teeth 92 provided on an extension element 94 that extends inwardly from the inner side of the trigger 24. When the trigger locking element 28 is pushed forward in the distal direction, the tang 90 engages the teeth 92 of the extension element 94 to prevent unintended movement of the trigger 24. In some embodiments, the trigger locking element 28 remains in position, preventing pivoting of the trigger 24, due to the force imposed upon the trigger by the spring.

The right-side thumb slide 22 extends through a linear slot that extends along the length direction of the handle 14 and connects to an inner gear rack 96 that comprises multiple teeth 98. These teeth 98 mesh with the teeth 100 of a gear 102 that is mounted to a horizontal shaft 104 within the handle 14. Provided on an inner surface of the gear 102 is a peg 106 to which one of the retractor control wires 63 is affixed. As shown in FIG. 8, this retractor control wire 63 extends forwardly through the handle 14 to the actuation member 84, which has an internal passage 108 (see FIG. 9; control wires 61, 63 and elongated tube 29 omitted for clarity) through which the control wire passes into the tube 29. Notably, a further retractor control wire 63 (not visible in FIG. 8) operated by the left-side thumb slide 22 shown in FIG. 1 can also pass through this passage 108. When either thumb slide 22 is moved in the proximal direction, its gear rack 96 is likewise moved in the proximal direction, which causes clockwise rotation (in the orientation of FIG. 8) of its associated gear 102. This, in turn, causes the associated retractor control wire 63 to be linearly displaced in the distal direction, which, in turn, causes lateral displacement of the retractor link to which the wire is attached and, therefore, bending of the retractor 12.

As noted above, the thumb slides 22 can also be locked in any desired position to fix the orientation of the retractor 12. This is achieved using the thumb slide locking element 26 (see FIG. 1). This locking element 26 extends through another slot that extends along the length direction of the handle 14. When the locking element 26 is moved in the proximal direction, it can move a spring element (not shown) that passes between opposed protrusions 110 and 112 extending from the handle 14 into engagement with the teeth 100 of the gear 102 so as to prevent its rotation and, therefore, prevent unintended articulation of the retractor 12.

Figure 9:
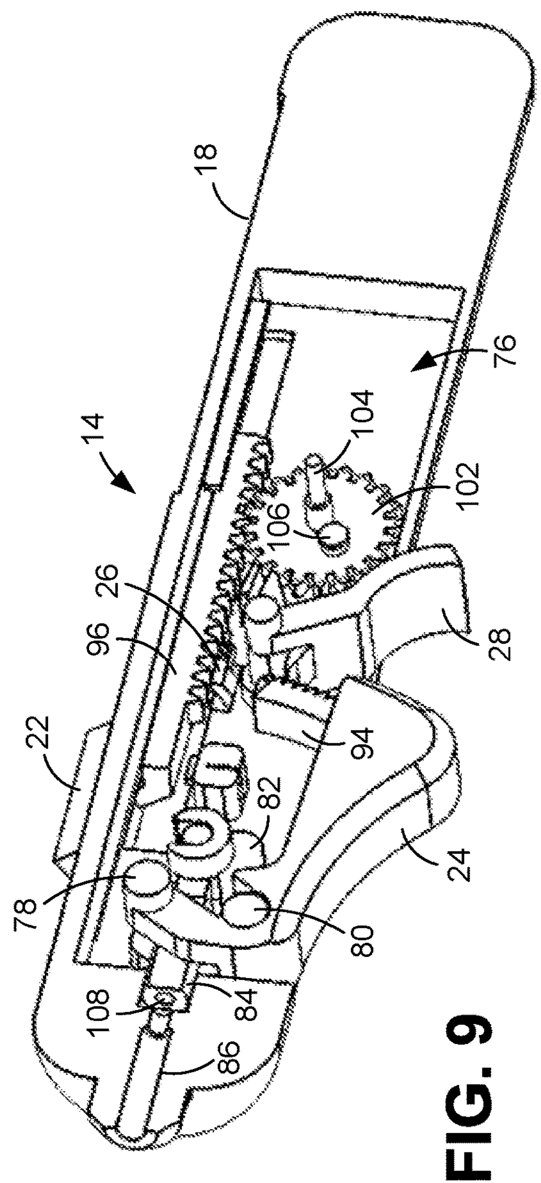
FIG. 9 is a cross-sectional perspective view of the handle of FIG. 8.

While FIGS. 8 and 9 only show the right-side thumb slide 22, gear rack 96, gear 102, retractor control wire 63, and locking element 26, it is noted that the left side of the handle comprises similar components. It is through duplication of these components that the retractor 12 can be manipulated to form complex curves comprising two different bends. As described above in relation to FIG. 4, one of the retractor control wires 63 connects to the distal articulable link 32. The other retractor control wire 63 connects to one of the medial articulable links 30, which is proximal of the distal articulable link 32. Accordingly, a first, distal bend can be formed with one of the retractor control wires 63 and a second, proximal bend can be formed with the other retractor control wire 63.

The invention claimed is:

1. An articulable endoscopic instrument comprising:

an articulable retractor configured to pass through a working channel of an endoscope, the articulable retractor comprising multiple articulable links that are connected together, a proximal end, and a distal end;

an end effector configured to pass through the working channel of the endoscope, the end effector being mounted to the distal end of the articulable retractor;

a tube configured to pass through the working channel of the endoscope, the tube comprising a proximal end and a distal end, the proximal end of the articulable retractor being mounted to the distal end of the tube;

a handle to which the proximal end of the tube is mounted, the handle comprising a housing that contains controls that enable a user of the instrument to both articulate the retractor and actuate the end effector, wherein the retractor can be articulated using the controls to form independent bends lying within one plane, the bends together forming a complex curve; and first and second retractor control wires that extend from the handle and through the articulable links, wherein linear movement of the retractor control wires causes the retractor to bend, wherein the first retractor control wire is connected to a distal articulable link of the retractor and the second retractor control wire is connected to a proximal articulable link of the retractor and wherein linear movement of the first retractor control wire causes the retractor to form a distal bend of the complex curve and wherein linear movement of the second retractor control wire causes the retractor to form a proximal bend of the complex curve, wherein the handle further comprises first and second thumb slides, wherein linear movement of the first thumb slide causes linear movement of the first retractor control wire and wherein linear movement of the second thumb slide causes linear movement of the second retractor control wire, wherein the handle further comprises first and second inner gear racks to which the first and second thumb slides are respectively connected and first and second gears having teeth that respectively engage teeth of the first and second gear racks, wherein the first and second retractor control wires are respectively connected to the first and second gears such that rotation of the gears causes linear movement of the retractor control wires, wherein the handle further comprises first and second thumb slide locking elements configured to respectively lock the first and second thumb slides to prevent unintended movement of the first and second retractor control wires, and wherein the first and second thumb slide locking elements comprise further thumb slides and wherein the handle further comprises spring elements connected to the further thumb slides, wherein respective linear movement of the further thumb slides toward the first and second gears causes the spring elements to engage the gears and prevent their rotation.

2. The instrument of claim 1, wherein the end effector comprises a grasper having jaw elements that can be opened and closed.

3. The instrument of claim 2, wherein the handle further comprises a finger trigger that can be used to open and close the jaw elements.

4. The instrument of claim 3, further comprising an end effector control wire and wherein pivoting of the finger trigger causes linear movement of the end effector control wire that causes opening and closing of the jaw elements.

5. The instrument of claim 4, wherein the end effector further comprises an actuation member connected to the jaw elements to which the end effector control wire is connected, wherein proximal movement of the end effector control wire causes proximal movement of the actuation member, which causes the jaw elements to close.

6. The instrument of claim 4, wherein the handle further comprises a spring that urges the finger trigger in a direction that opens the jaw elements.

7. The instrument of claim 4, wherein the handle further comprises a finger trigger locking element configured to lock the orientation of the finger trigger to prevent unintended movement of the end effector control wire.

8. The instrument of claim 7, wherein the finger trigger locking element comprises a pivotally mounted lever having a tang configured to engage teeth of an extension element that extends from the finger trigger.

9. The instrument of claim 1, further comprising an elongated tube that connects the retractor to the handle, the elongated tube also being configured to pass through the working channel of the endoscope.

* * * * *